US012735450B2

(12) United States Patent
Fauerbach et al.

(10) Patent No.: US 12,735,450 B2
(45) Date of Patent: Sep. 15, 2026

(54) SERUM RESISTANT BIS-SULFHYDRYL SPECIFIC BIOTINYLATION REAGENT

(71) Applicant: Miltenyi Biotec B.V. & Co. KG, Bergisch Gladbach (DE)

(72) Inventors: Jonathan Fauerbach, Bergisch Gladbach (DE); Tina Borke, Bergisch Gladbach (DE); Jörg Mittelstaet, Bergisch Gladbach (DE); Sandra Dapa, Bergisch Gladbach (DE)

(73) Assignee: Miltenyi Biotec B.V. & Co. KG, Bergisch Gladbach (DE)

( * ) Notice: Subject to any disclaimer, the term of this patent is extended or adjusted under 35 U.S.C. 154(b) by 604 days.

(21) Appl. No.: 18/111,634

(22) Filed: Feb. 20, 2023

(65) Prior Publication Data

US 2023/0357313 A1 Nov. 9, 2023

(51) Int. Cl.
*C07K 1/107* (2006.01)
*C07D 495/04* (2006.01)

(52) U.S. Cl.
CPC .......... *C07K 1/1077* (2013.01); *C07D 495/04* (2013.01)

(58) Field of Classification Search
CPC ............................ C07K 1/1077; C07D 495/04
See application file for complete search history.

(56) References Cited

FOREIGN PATENT DOCUMENTS

EP 3 878 464 9/2021

OTHER PUBLICATIONS

Del Rosario R B et al. "Streptavidin-biotinylated IgG conjugates: a simple procedure for reducing polymer formation" International Journal of Radiation, pp. 417-421.

*Primary Examiner* — Erich A Leeser
(74) *Attorney, Agent, or Firm* — Jaquelin K Spong

(57) ABSTRACT

Biotinylation reagent has a structure according to formula (I)

(I)

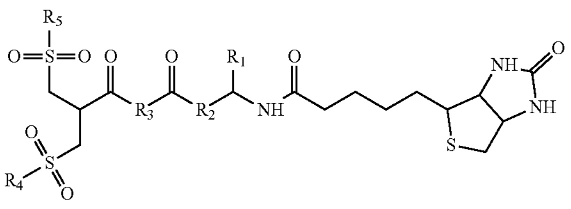

With
R1=alkyl, hydroxyalkyl or carboxyalkyl residue comprising 1 to 50 carbon atoms
R2=alkyl, glycol, amine or peptide reside with 1 to 50 carbon atoms
R3=Aryl, heteroaryl, with 3 to 50 carbon atoms
R4, R5=Aryl, hetero-aryl, Alkyl with 3 to 50 carbon atoms
Use of the agent in cell separation processes.

4 Claims, 3 Drawing Sheets

SERUM RESISTANT BIS-SULFHYDRYL SPECIFIC BIOTINYLATION REAGENT

CROSS REFERENCE TO RELATED APPLICATIONS

This UN nonprovisional patent application claims priority to European patent application Serial No. EP22158475.8 filed in the European Patent Office on Feb. 24, 2022. This prior application is incorporated by reference in its entirety, for all purposes.

STATEMENT REGARDING FEDERALLY SPONSORED RESEARCH

Not applicable.

STATEMENT REGARDING MICROFICHE APPENDIX

Not applicable.

BACKGROUND

Antibodies and Antibody-fragments are commonly used for whole-blood products in in-vitro applications as well as for in-vivo and clinical applications to target specific cellular targets.

Biotinylation of these biomolecules is often used to introduce a tag or handles so that they can be recognized by a secondary recognition system, based for example on Streptavidin, Avidin or anti-Biotin Antibody to name a few.

Various biotinylation reagents are known and for example disclosed in Liberatore et al., Bioconjugate Chem. 1990, 1, 36-50, doi: 10.1021/bc00001a005, EP3620464A1 or D. M. Mock & A. Bogusiewicz; pp. 209; From: Methods in Molecular Biology, vol. 418: Avidin-Biotin Interactions, Methods and Applications.

From a different technology field, crosslinking a disulfide bridge of an antibody is known. For example the chemistry of recognition of two neighboring reduced thiols previously forming a disulfide bridge was first described in a scientific publication in 1979 at Sumita Mitra et al. "Reagents for Cross-Linking of Proteins", JACS 101211 (1979), Liberatore F. et al. Bioconjugate Chem, 1, (1990), and Rosario et al. Bioconjugate Chem, 1990, 1, 51-59; where the cross-linker was referred to as: equilibrium transfer alkylation crosslinker (ETAC). It is described that a full antibody is reacted with a cross linker for the purpose of labeling the antibody with a fluorescent dye. Another scientific publication describes a similar use on a Fab (Wilbur et al., Bioconjugate Chem 1994, 5, 220-235).

US 2016/0000933 A1 discloses the crosslinking of antibodies at their disulfide bridge for the preparation of antibody conjugates.

Further publications pertinent to crosslinking of antibodies at their disulfide bridge are for example WO 2016/168769 A1; HANIEH KHALILI ET AL: "Comparative Binding of Disulfide-bridged PEG-Fabs". BIOCONJUGATE CHEMISTRY, vol. 23, no. 11, 21 Sep. 2012 (2012-09-21), pages 2262-2277; Greg T. Hermanson: "Antibody Modification and Conjugation" In: "Bioconjugate Techniques", 1 Jan. 2013 (2013-01-01), Academic Press, ISBN: 978-0-12-382239-0 pages 867-920; WO 2016/154621 A1

In serum-related applications of biotinylated antibodies (e.g. in-vivo and whole-blood in-vitro applications), the Biotin tag needs to be resistant for several hours. Normal serum (human and mouse) contain factors, which break down biotinamides. An example of such a factor is the naturally occurring enzyme biotinidase enzyme. This natural enzyme is able to break down biotin amides, releasing free biotin and the amine.

It was therefore an object of the invention to provide a chemically well-defined serum-resistant adapter molecule with an univariant number of tag/affinity units (e.g. Biotin) per Ab and/or Fab on site-specific positions.

SUMMARY

Here we describe the synthesis of a new biotinylation reagent which is resistant to human Serum and enzymatic degradation (e.g. by Biotinidase among other factors). Without being bound to this theory, this is thanks to the presence of a carboxylic group in alpha to the amide bond which specifically prevents degradation.

The reagent of the invention specifically reacts with two sulfhydryl groups. This makes it particularly attractive to target reduced disulfides in proteins (e.g. Antibodies) without loss of structure or stability of the biomolecule, as the reagent is able to re-bridge the sulfhydryl groups. Such Biotinylated-Antibodies or antibody fragments are therefore suitable for any application where biotin conjugates are exposed to blood, bloodproducts, fresh serum or plasma samples, which have not been treated in a way to reduce or inhibit activity of factors, which break down biotinamides in particular also clinical applications where Biotin is used as a tag.

The invention is based on using a site-directed crosslinker that targets disulfide bonds on Ab and/or Fabs. The benefit relies on: i) specific location of disulfide bridge, which is known in the sequence and structure of Ab and Fabs at fixed positions; ii) the crosslinker covalently attaches to both reduced thiols of the disulfide bridge, thus preserving the native 3D structure and function of the Ab and Fab leaving no free thiols behind; iii) each crosslinker carries only one tag or affinity unit moiety (e.g. Biotin or Thiamine), so for each disulfide bridge will be modified by linker carrying one biotin providing a known and predictable stoichiometry (i.e. fabs only contain one disulfide bridge at the C-terminal); iv) the crosslink reaction is quantitative, meaning above 95% of Ab and Fab is labeled; v) degree of labeling can be stoichiometric controlled (i.e. for Ab); vi) the crosslink conjugate is insensitive to thiol reduction and reducing environments.

Accordingly, object of the invention is a biotinylation reagent according to formula (I)

(I)

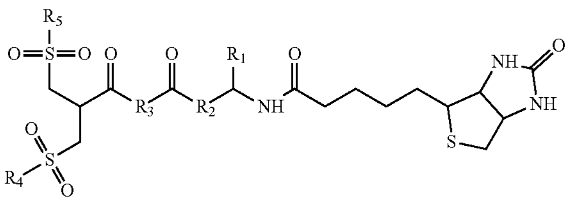

With R1=alkyl, hydroxyalkyl, carboxyalkyl residue comprising 1 to 50 carbon atoms, preferable comprising at least one O or N atoms, e.g. —OH, —$CO_2$H, —$CH_2CH_3$, —$CH(CH_3)_2$, —$OCH_3$, —$CH_2$OH;

R2=alkyl, glycol, amine or peptide reside with 1 to 50 carbon atoms, preferable having a molecular weight less than 150 kDa;

R3=Aryl, hetero-aryl, with 3 to 50 carbon atoms

R4, R5=Aryl, hetero-aryl, Alkyl with 3 to 50 carbon atoms

DETAILED DESCRIPTION

Figure 1:
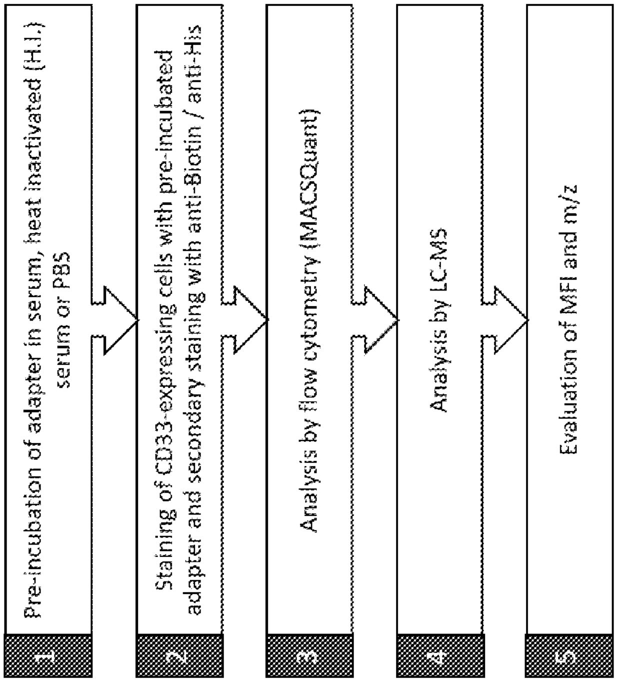
FIG. 1 shows the workflow designed for assessment of the serum stability for all linker molecules

The groups R1-R5 of the biotinylation reagent may stand for the following residues:

R1 $-CO_2H$, $-CH_2CO_2H$, $-CH_3$, $-C_2H_5$, $-C_3H_7$, $-CH-(CH_3)_2$, $-C_4H_9$, $-CH_2OH$, $-C_2H_4OH$, $-C_3H_6OH$,

R2 Alkyl amine or di amine organic chain, optionally substituted, like $NH-(CH_2)_4$; $NH-(CH_2)_5$; $NH-(CH_2)_6$, $-NH-(CH_2)_2-NH-CO$; $-NH-(CH_2)_3-NH-CO$; $-NH-(CH_2)_4-NH-CO$;

R3 Aromatic organic compound and derivatives, preferable 5 or 6 membered carbon ring, with two carbonyl residues in para and optionally additionally substituted, preferentially without substitution, e.g. Benzene, R4, R5 Aromatic organic compound and derivatives, typically 5 or 6 member carbon ring, optionally substituted in ortho, metha and/or para position, preferentially in para potion with alkyl carbon chain, like benzene, toluene, ethyl benzene, mesitylene More preferable, the biotinylation reagent according to the invention has the substitution pattern of formula (II), (III) or (IV)

(II)

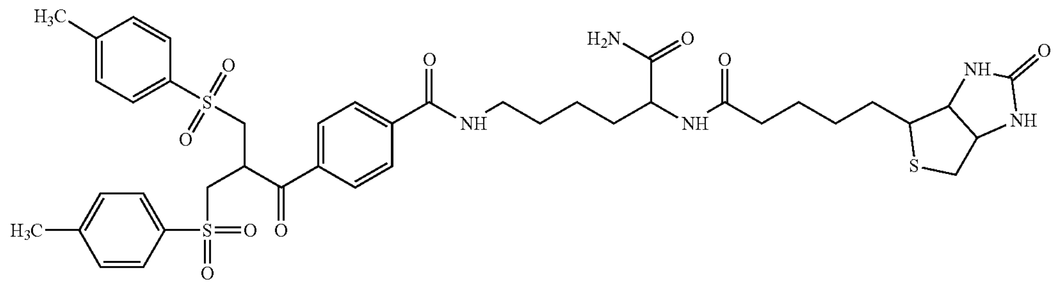

(III)

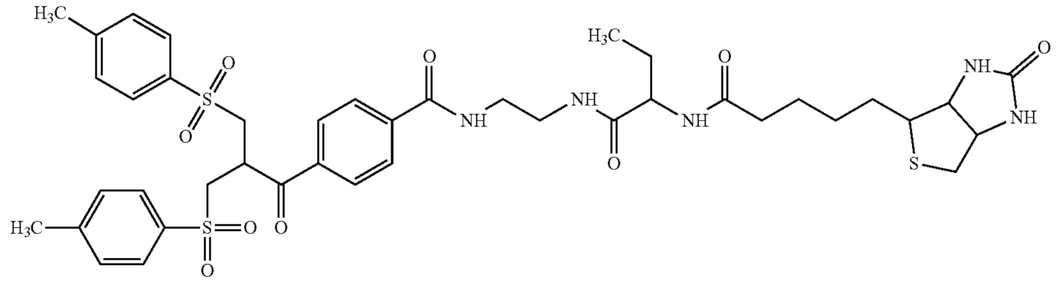

(IV)

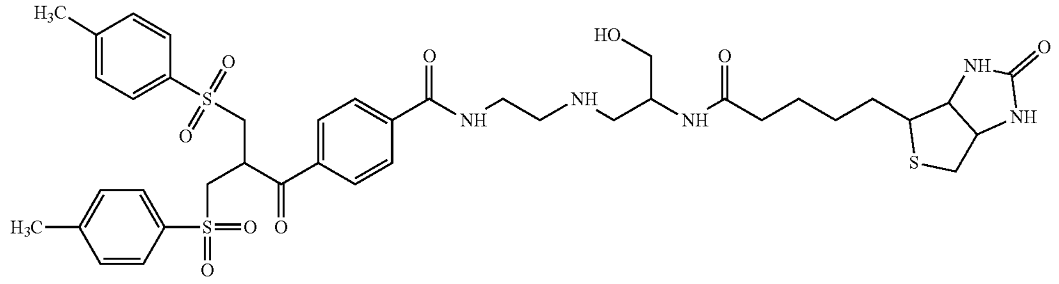

-continued (V)

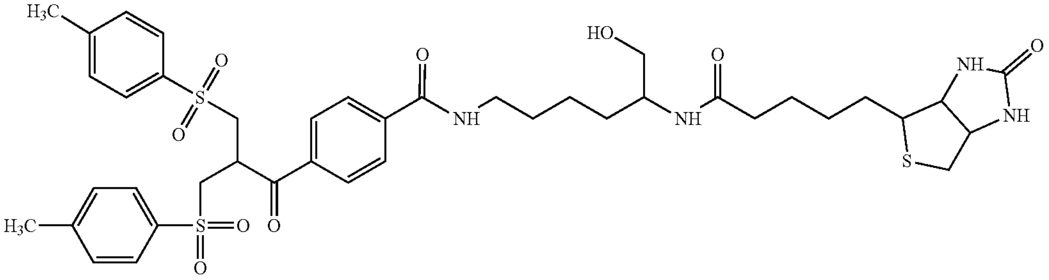

The biotinylation agent according to the invention is especially useful for biotinylation of antigen binding molecules having an antigen binding domain comprising a heavy chain and a light chain connected by a sulphur atom-linker-sulphur atom bridge.

The term "antigen recognizing domain" refers to any kind of antibody, fragmented antibody or fragmented antibody derivatives, directed against a target moiety expressed on a biological specimen of interest. The term relates to fully intact antibodies, fragmented antibody or fragmented antibody derivatives, e.g., Fab, Fab¢, F(ab¢)2, sdAb, scFv, di-scFv, nanobodies. Such fragmented antibody derivatives may be synthesized by recombinant procedures including covalent and non-covalent conjugates containing these kind of molecules. Further examples of antigen recognizing moieties are peptide/MHC-complexes targeting TCR molecules, cell adhesion receptor molecules, receptors for costimulatory molecules, artificial engineered binding molecules, e.g., peptides or aptamers which target, e.g., cell surface molecules.

Preferable, the term "Antigen recognizing domain" refers to a moiety directed against antigen expressed by the biological specimens (target cells) extracellular, like IL2, FoxP3, CD154, CD33 (Siglec-3), CD123 (IL3RA), CD135 (FLT-3), CD44 (HCAM), CD44V6, CD47, CD184 (CXCR4), CLEC12A (CLL1), LeY, FRβ, MICA/B, CD305 (LAIR-1), CD366 (TIM-3), CD96 (TACTILE), CD133, CD56, CD29 (ITGB1), CD44 (HCAM), CD47 (IAP), CD66 (CEA), CD112 (Nectin2), CD117 (c-Kit), CD133, CD146 (MCAM), CD155 (PVR), CD171 (L1CAM), CD221 (IGF1), CD227 (MUC1), CD243 (MRD1), CD246 (ALK), CD271 (LNGFR), CD19, CD20, GD2, EGFR, and CD33. These antigen may also be soluble antigens specifically associated with the TME e.g. arginase, carcinoembryonic antigen, CCL11, CCL18, CCL2, CCLS, CD282, Circulating Tumor Nucleic Acids, CXCL10, FAP, GM-CSF, IFN-γ, IL-4, IL-6, IL-7 IL-8, IL-10, IL-11, IL-12, 11-13, IL-14, IL-15, IL-17, IL-23, IL-33, IL-1beta, IL-1Ra, INF, LAP, M-CSF, MMP12, MMP13, MMP7, NY-ESO-1 antibody, prostate-specific antigen, sCD106, sCD137, sCD152, sCD223, sCD25, sCD27, sCD253, sCD270, sCD273, sCD274, sCD279, sCD28, sCD30, sCD366, sCD40, sCD54, sCD80, sCD86, sGITR, TGFβ-1, TGFβ-2, TGFβ-3, TIMP1 or TNF-α, VEGF. The "s" in sCDx regularly stands for a soluble form of the respective CDx molecule.

USE OF THE INVENTION

Further objects of the invention are the use of the biotinylation reagent as defined above or a method of using the biotinylation reagent as defined above for biotinylation of a protein or peptide containing at least one disulfide bond.

This protein may contain an antigen binding moiety, resulting in a protein or peptide where the disulfide bond is replaced and reconstituted by a 3-carbon linker bridge originating from the biotinylation agent.

In another variant, the protein comprises an antibody fragment (FAb) unit and the disulfide bond modified by the biotinylation agent is the interchain disulfide bond. Preferable, the protein contains an antigen binding moiety, resulting in a protein or peptide where the disulfide bond is replaced and reconstituted by a 3-carbon linker bridge originating from the biotinylation agent.

In another variant, the protein comprises at least two amino acids with Sulphur atoms and wherein the at least two amino acids are linked by the biotinylation agent.

The biotinylated proteins may be used as antigen binding molecule in a cell separation workflow by immunomagnetic separation or as antigen binding molecule in a cell separation workflow by flow sorting separation. In this cell separation workflow, which target cells may be separated from non-target cells from whole blood or whole-blood products or from media containing non-heat inactivated serum or plasma or active biotinidase.

EXAMPLES

Human and murine blood was drawn on the same day of the experiment and collected in serum cloth activator tubes. After 30 min of incubation at RT (room temperature), the tubes were centrifuged at 2200×g for 15 min. The top layer which contained the human serum was removed carefully and transferred into a fresh tube. To remove antibodies from the serum, which would interfere with the later LC-MS analysis, the serum was diluted 1:1 with PBS and loaded onto a protein A column (Thermo Fisher Scientific, Order-Nr.:20356) equilibrated with PBS. The flow through, was collected in a fresh tube. For the H.I. (heat inactivated) serum control a part from the IgG free serum was transferred into an Eppendorf tube and incubated for 30 min at 56° C. After the pre-incubation the samples were divided, one part was used for a staining and analyzed via MACSQuant, the remaining samples were purified and analyzed via LC-MS.

The biotinylated anti-CD33 Fabs were incubated in PBS, or in the freshly prepared serum for 1 at 37° C. in a concentration of 0.1 μg/μl.

For the staining $1\times10^4$ CD33-expressing OCI-AML-2 cells per well were incubated with 10 μl pre-incubated Fabs, as described above, for 10 min at 4° C. A washing step with PEB buffer (1×PBS/5 mM EDTA/0.5% Serum) and a subsequent secondary staining was performed, in which the OCI-AML-2 cells were stained with either an anti-Biotin (Miltenyi Biotec: 120-000-898) or an anti-His antibody (Miltenyi Biotec: 120-047-112) and 7-AAD (Miltenyi Biotec: Order-Nr.: 130-111-569). Finally, cells were washed with PEB Buffer and analyzed using the MACSQuant Analyzer 10.

Figure 2:
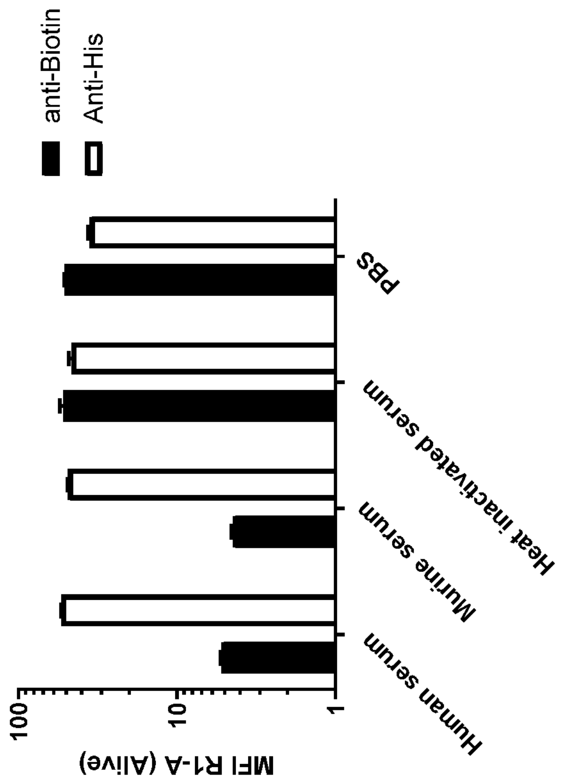
FIG. 2 shows the serum stability of the original and unmodified linker MS9 molecule in both human and murine serum by cell staining

FIG. 2 shows the results of serum stability test comparing human and murine serum. Biotinylated anti-CD33 FAbs were incubated for 1 h in freshly prepared human serum, murine serum, heat inactivated human serum or PBS. Presence of the FAb moiety (anti-His) and biotin-moiety (anti-Biotin-PE, (middle panel)) on cell bound (OCI-AML2) anti-CD33 Fabs, was determined by multicolor flow-cytometry. MFI (mean fluorescence intensity) is shown for n=3 technical replicates.

Furthermore, different linker moieties (MS12, MS13, MS14 or MS15) were tested and the pre-incubation period was prolonged to 4 hours.

Therefore, anti-CD33 Fabs with different linker moieties (MS9, MS12, MS13, MS14 or MS15) were incubated in PBS, or in the freshly prepared serum for 4 hours at 37° C. in a concentration of 0.1 μg/μl.

For the staining $1\times10^4$ CD33-expressing OCI-AML-2 cells per well were incubated with 10 μl pre-incubated Fabs, as described above, for 10 min at 4° C. A washing step with PEB buffer (1×PBS/5 mM EDTA/0.5% Serum) and a subsequent secondary staining was performed, in which the OCI-AML-2 cells were stained with either an anti-Biotin (Miltenyi Biotec: 120-000-898)/Strepdavidin-PE (Miltenyi Biotec: 120-045-655) or an anti-His antibody (Miltenyi Biotec: 120-047-112) and 7-AAD (Miltenyi Biotec: Order-Nr.: 130-111-569).

Finally, cells were washed with PEB Buffer and analyzed using the MACSQuant Analyzer 10

To prepare the samples for an analysis via LC-MS, the pre-incubated adapters were purified via an IgG-CH1 Affinity matrix (Thermo Fisher: 194320005), therefore 25 uL of CH1-resin were transferred into a 1.5 mL microcentrifuge tube for each sample, all further steps were performed according to the manufacturer's protocol.

Figure 3:
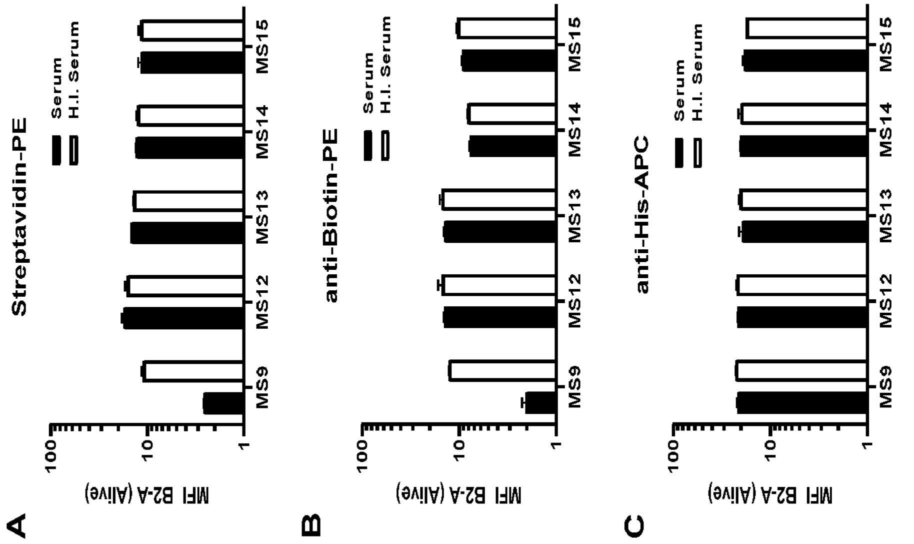
FIG. 3 shows the serum stability screening for all linker molecules and positive outcome for the modified linkers (MS12, MS13, MS14 and MS15) by cell staining

FIG. 3 shows the results of serum stability test. Presence of the Biotin-moiety (Streptavidin-PE (panel A and anti-Biotin-PE, panel B)) and FAb moiety (anti-His APC, Panel C) on cell bound (OCI-AML2) anti-CD33 FAbs was determined by multicolor flow-cytometry. MFI (mean fluorescence intensity) is shown for n=2 technical replicates. A marked decrease in anti-Biotin staining intensity was observed for MS9-modified FAbs incubated in non-heat inactivated serum (serum) but not for MS12-, MS13-, MS14-, or MS15-modified FAbs.

To verify that biotinidase, an enzyme found in the human body amongst other in human serum, causes the cleavage of the biotinamide bond an experiment was performed with a biotinidase inhibitor ((+) Biotin 4 Amidobenzoic Acid, Cayman, CAS. 102418-74-6). Therefore (+) Biotin 4 Amidobenzoic Acid was added at a concentration of 1 mM into the pre-incubation mix containing the human serum. As control no inhibitor was added. The anti-CD33 Fab with MS9 was pre-incubated for 4 hours at 37° C. Subsequently after the incubation the samples were purified via an IgG-CHI Affinity matrix as previously described.

Synthesis

Synthesis of Bis-sulfone NHS-ester, 2

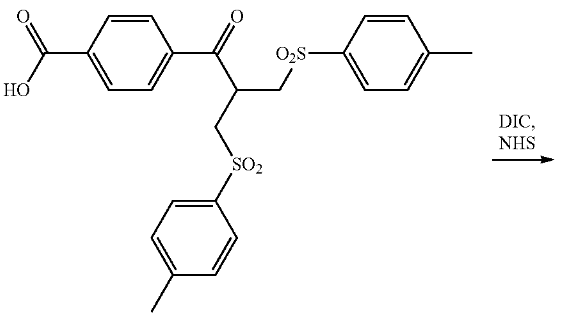

1

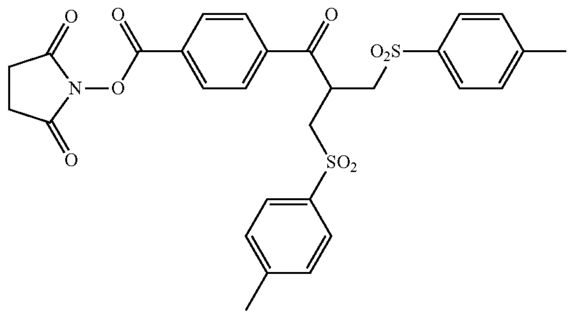

2

The synthesis (4-[2,2-bis([p-tolylsulfonyl)methyl]acetyl] benzoic acid) 1 was reported by Liberatore et al. (Bioconjugate Chem. 1990, 1, 36-50, doi: 10.1021/bc00001a005). Bis-sulfone 1 (1 eq.) was dissolved in dry tetrahydrofuran (THF, 100 mg/mL) under a blanket of nitrogen. N-Hydroxysuccinimide (NHS, 1.5 eq.) was added and the mixture was cooled in an ice bath. Diisopropylcarbodiimide (DIC, 1.5 eq.) was added dropwise at 0° C. After about 10 min the mixture was allowed to come to room temperature. The product precipitated as a white solid forming a suspension. The reaction was complete after about 30 min, as followed by thin layer chromatography.

The product was dissolved in methylene chloride and extracted with water. The organic phase was dried over anhydrous sodium sulfate, then filtered and concentrated in vacuo to give 2 as a white powder.

Synthesis of $N^{\varepsilon}$-(biotinamido)-L-lysine, 4

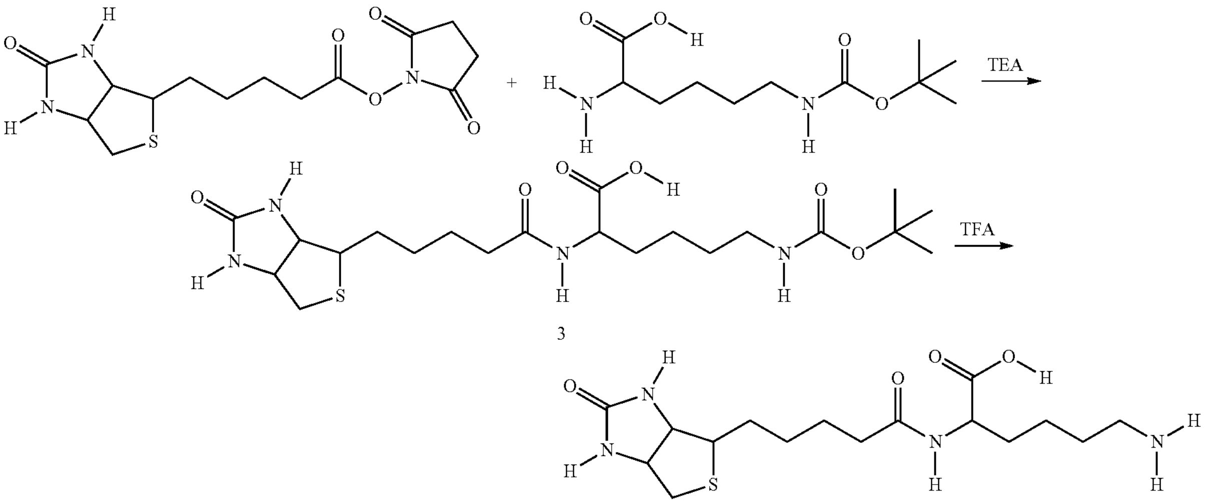

3

4

$N^{\varepsilon}$-Boc-L-lysine (1.0 eq.) was dissolved in dry dimethylformamide (DMF, 20 mg/mL) in a nitrogen atmosphere. 1.5 eq. of triethylamine (TEA) were added. Biotin-NHS (1.5 eq.) was dissolved in dry DMF (20 mg/mL) and add dropwise under stirring to the lysine solution under a blanket of nitrogen. The mixture was stirred at room temperature for 16 h to give compound 3.

3 was deprotected by addition of trifluoroacetic acid (TFA, 60 eq.) and stirred at room temperature for 3 h, before being concentrated in vacuo. The biotinylated lysine 4 was isolated by precipitation of its ammonium salt. Therefore, the concentrated crude reaction mixture was diluted with ethanol in presence of ammonium hydroxide. The white precipitate was collected by filtration.

Synthesis of $N^{\varepsilon}$-(biotinamido)-$N^{\alpha}$-(4-[2,2-bis[(p-tolylsulfonyl) methyl]acetyl]benzamido)-L-lysine, 5 (MS 12)

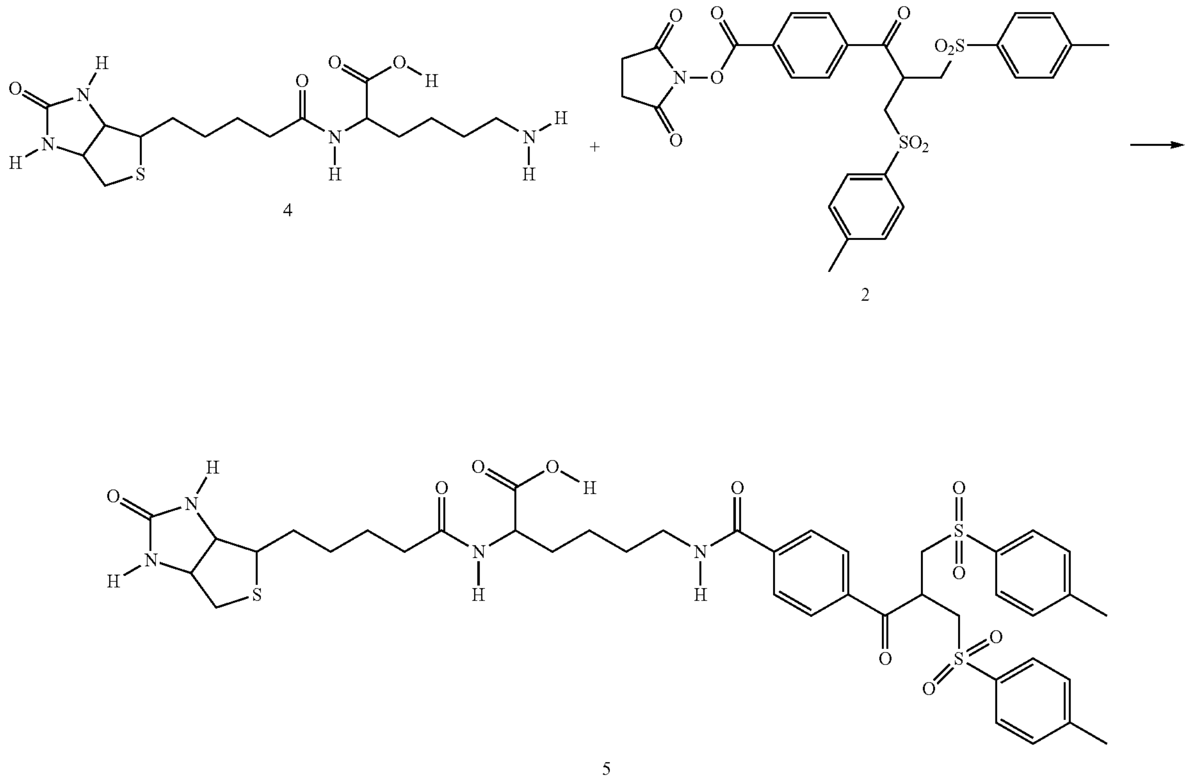

4

2

5

The biotinylated lysine 4 (1.0 eq.) was dissolved in dry DMF (20 mg/mL) in a nitrogen atmosphere. Bis-sulfone NHS ester 2 (1.10 equivalent) was dissolved in dry DMF (50 mg/mL) and added dropwise under stirring to the biotin solution under a blanket of nitrogen. The mixture was stirred at room temperature for 16 h, then concentrated in vacuo and purified by preparative reverse phase (C18) liquid chromatography using a gradient of 100% water+0.1% TFA→100% acetonitrile+0.1% TFA. The target fraction was lyophilized to obtain 5 as a white powder.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:

1. A method for use of a biotinylation agent for biotinylation of a protein or peptide containing at least one disulfide bond comprising:

reacting the biotinylation agent according to formula (I)

(I)

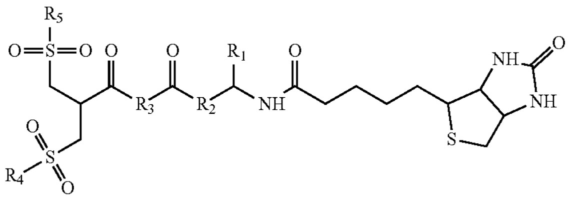

With

R1=alkyl, hydroxyalkyl or carboxyalkyl residue comprising 1 to 50 carbon atoms

R2=alkyl, glycol, amine or peptide reside with 1 to 50 carbon atoms

R3=Aryl, heteroaryl, with 3 to 50 carbon atoms

R4, R5=Aryl, hetero-aryl, Alkyl with 3 to 50 carbon atoms reducing at least one disulfide bond of the protein or peptide;

reacting the resulting free thiols with a biotinylation reagent according to formula (I) in a suitable buffer (e.g., PBS, pH 6-8) at a temperature between 4° C. and 37° C. for 0.5-18 hours, thereby re-bridging the original disulfide via a three-carbon linker and attaching one biotin moiety per modified disulfide; and optionally removing excess reagent and/or purifying the biotinylated conjugate.

2. The method of claim 1, wherein the protein contains an antigen binding moiety, resulting in a protein or peptide where the disulfide bond is replaced and reconstituted by a 3-carbon linker bridge originating from the biotinylation agent.

3. The method of claim 1, wherein the protein comprises an antibody fragment (FAb) unit and the disulfide bond modified by the biotinylation agent is the interchain disulfide bond.

4. The method of claim 1, wherein the protein comprises at least two amino acids with Sulphur atoms and wherein the at least two amino acids are linked by the biotinylation agent.

* * * * *